United States Patent [19]

Shanbrom

[11] 4,188,318

[45] Feb. 12, 1980

[54] SIMPLIFIED METHOD FOR PREPARATION OF HIGH YIELD, HIGH PURITY FACTOR VIII CONCENTRATE

[76] Inventor: Edward Shanbrom, 2252 Liane La., Santa Ana, Calif. 92700

[21] Appl. No.: 899,235

[22] Filed: Apr. 24, 1978

Related U.S. Application Data

[63] Continuation of Ser. No. 586,948, Jun. 16, 1975, abandoned.

[51] Int. Cl.² .............................................. A61K 37/02
[52] U.S. Cl. ................................. 260/112 B; 424/101
[58] Field of Search ...................... 260/112 B; 424/101

[56] References Cited

U.S. PATENT DOCUMENTS

3,973,002   8/1976   Hagan .............................. 260/112 B

OTHER PUBLICATIONS

John T. Edsall, J. Amer. Chem. Soc., vol. 77, 1955, pp. 157–161.
M. W. Mosesson, J. Biol. Chem., vol. 245, No. 21, 1970, pp. 5728–5736.

*Primary Examiner*—Paul R. Michl
*Attorney, Agent, or Firm*—Knobbe, Martens, Olson, Hubbard & Bear

[57] ABSTRACT

A method for concentrating and purifying Factor VIII by selective cold precipitation in low ionic strength solution is disclosed.

1 Claim, No Drawings

SIMPLIFIED METHOD FOR PREPARATION OF HIGH YIELD, HIGH PURITY FACTOR VIII CONCENTRATE

This is a continuation of application Ser. No. 586,948, filed June 16, 1975, now abandoned.

Several different methods have been described for the production of antihemophilic factor (AHF or Factor VIII) for therapeutic use, e.g., selective precipitation, batch absorption and elution, extraction in low ionic media and chromatography. Chemicals most frequently used for precipitation include alcohol, tannic acid, ammonium sulfate, glycine, and polyethylene glycol. While purification of Factor VIII entails the elimination of a variety of other plasma proteins, fibrinogen is by far the most important and troublesome of these proteins, particularly when denatured by such processes as alcohol precipitation, freezing and thawing. This denatured fibrinogen impairs filtration of AHF, causes appreciable losses of AHF during purification steps and decreases the solubility of the lyophilized product in reconstituting fluid. Thus, any satisfactory method of purifying AHF requires removal of appreciable quantities of fibrinogen. The selective precipitation techniques described above are designed for this purpose but all have the disadvantages of either further denaturing fibrinogen and AHF or producing undesirable losses of AHF.

Methods utilizing simple cold precipitation without chemicals (cryoprecipitation) are limited to small scale production usually in blood blanks, and result in high fibrinogen blood levels when used therapeutically, a feature considered undesirable by some experts in the field.

Procedures which involve the extraction of Factor VIII from cryoprecipitate in low ionic strength buffers, while decreasing fibrinogen content of the final product somewhat, still have an undesirably high protein content, require special equipment and procedures for centrifugation and are limited in the total amount of AHF which may be extracted from the cryoprecipitate without impairing purification.

Other problems commonly associated with large scale manufacture of AHF are the contamination by pyrogenic substances and viruses which cause hepatitis (hepatitis associated antigen, HAA) of the final product. With chemical precipitants these undesirable contaminants may actually be enhanced.

The method herein described virtually eliminates these problems, lacks the disadvantages associated with chemical precipitants and relies on the simple procedure of selective cold precipitation of fibrinogen, its denatured and degraded products. (Reference to removal of fibrinogen hereinafter includes removal of fibrinogen and its denatured and degraded products.)

The selective precipitation of fibrinogen without associated loss of Factor VIII has not been previously accomplished as a practical method for large scale manufacture of a purified AHF concentrate. In fact Wickerhauser (1), emphasizes the importance of limiting the time and temperature in extracting AHF. "Somewhat higher yields of AHF were obtained by prolonged Tris extraction at 30° C. beyond 60 minutes, but the extract was increasingly contaminated with aggregated fibrinogen which made the final concentrate poorly filterable. Conversely, lower and variable AHF yields were obtained at shorter extraction, or at lower temperature." The procedure herein described eliminates all of these problems because any excessive fibrinogen contamination is removed during the cooling, while none of the AHF is lost.

While the effect of cooling has been previously noted by Hershgold et al (2) they required 18 to 30 hours at 4° C. and failed to obtain or suggest the accelerated and selective precipitation of fibrinogen and isohemagglutinins at the lower temperature of 0°-2° C. (In fact, in later work Hershgold et al totally eliminate a cooling step in an attempt to produce very highly purified AHF (3).) The authors (2) admit that they were not able to produce a therapeutic concentrate which could be consistently sterile filtered and they had to resort to further steps of alcohol or glycine precipitation. The striking improvements of the present invention were an unexpected surprise in view of the discouraging reports of Hershgold and others.

James and Wickerhauser (5) comment "Furthermore, since the method has to be carried out at room temperature to avoid precipitation of fibrinogen," but they failed to develop any procedure to produce a Factor VIII concentrate using the principles of this invention. Their final product was also much lower in yield and purity compared to that described in this invention. Further processing with PEG to remove fibrinogen and increase purity resulted in even more striking losses of Factor VIII. (1,6)

Thus, it appears that other workers have long assumed or concluded from their experience that there were no particular improvements in results to be expected from the use of the only slightly lower temperatures used in the precipitation and removal of fibrinogen, after only a very short precipitating time. The unexpected and vastly improved results found and reported here are contrary to the teachings and suggestions of the prior art, and were arrived at in initial stages by the inventor more by coincidence than by design.

This invention is a specific method for the large-scale manufacture of a Factor VIII concentrate. Among the more unique features of the invention is the selective cold precipitation of excessive amounts of fibrinogen, its denatured forms and degradation products in low ionic strength solution, without added chemicals, and without undesirable loss of AHF activity. An additionally outstanding feature is the surprisingly high yield of Factor VIII, approximately 25–40% of the theoretical plasma. In addition, and in spite of the high AHF recovery, the protein content has been reduced 50–75%, compared to other products. This is illustrated in Table I. The need for a high yield, high purity freeze-dried AHF concentrate has received international recognition and concern (7,8), and it is generally agreed that commercial concentrates usually yield less than 20% of the theoretical AHF present in plasma (7,8,9).

TABLE I[1]

SOME CHARACTERISTICS OF FACTOR VIII CONCENTRATES[2]

| Product | Units Factor VIII/ Ml | Total Volume Administered (Ml) | Total Units Factor VIII | Total Fibrinogen (GM) | Total Protein (GM) | Total Sodium (MEQ) | Total Chloride (MEQ) | Total Cost (Dollars) | Source |
|---|---|---|---|---|---|---|---|---|---|
| (1) Fresh frozen plasma | 0.3 | 8000 | 4000 | 8.0 | 240 | 1200 | 800 | 480 | Blood bank |
| (2) Cryoprecipitate | 10[3] | 400 | 4000 | 4.0 | 20 | 40 | 40 | 400 | Blood bank |
| (3) Factorate | 10 | 400 | 4000 | 0.8 | 14 | 96 | 80 | 480 | Armour pharmaceutical |
| (4) AHF | 10 | 400 | 4000 | —[4] | 20 | 80 | 48 | 480 | Abbott Laboratory |
| (5) Hemofil | 25 | 160 | 4000 | 1.0 | 5.6 | 25 | 20 | 528 | Hyland |
| (6) AHF[5] | 10 | 400 | 4000 | | 6.0 | | | | Shanbrom |
| (7) AHF[6] | 10 | 400 | 4000 | | 2.0 | | | | Shanbrom |

[1]This table, except for the "Shanbrom" entries are from "Recent Advances in Hemophilia" Ann. N.Y. Acad. Sciences 240:165-171, 1975, Robert T. Breckenridge. The Shanbrom entries result from the invention described herein.
[2]These figures are based upon the experience of the Hemophilia Center of Rochester and Monroe County and are expressed as totals necessary to treat a 70-kg patient to one unit per ml. They assume a recovery of 80% in vivo.
[3]Variable, but usually between 7-12 $\mu$/ml.
[4]Unable to measure fibrinogen due to precipitation at 37° C.
[5]Single step without further precipitation.
[6]Further precipitation by Polyol precipitation.

EXAMPLE METHOD

Frozen plasma, e.g., 100 to 3000 liters, are thawed at from about −5° C. to about +2° C. and collected in an appropriate tank or vessel. Greater volumes may be handled but operations become difficult. The cold insoluble fraction (cryoprecipitate) is collected, preferably in continuous flow centrifuges (Sharpless or similar centrifuges), at less than 3° C. Other collection methods may be used but are less efficient. The cryoprecipitate is weighed and then mixed with a small amount of distilled, pyrogen-free water, preferably in a Waring-type blender for a few seconds, to produce a slurry or emulsion. The slurry is then extracted in from 2 to about 3 volumes of distilled pyrogen-free water at about pH 7.0 for from about 30 to about 60 minutes after warming to 20°-30° C. Aluminum hydroxide gel is then added to the amount of from 10 to 30 ml. per liter and allowed to adsorb for 15 minutes. Tricalcium phosphate, 0.5-2.0%, by weight, may be added for further purification and the amount of aluminum hydroxide reduced. This step aids in the removal of lipids, denatured proteins and prothrombin complex. The entire procedure is carried out in a jacketed reaction vessel with continuous stirring, taking care to avoid foaming. The contents of the vessel is then cooled to internal temperature of from about 1° C. to about 2° C. for from about ½ to 2 hours. The heavy precipitate which forms is removed by continuous-flow centrifugation (e.g., Sharpless). The supernatant is stabilized with 0.02 molar trisodium citrate and 0.1 molar glycine at temperature of 20°-25° and the pH is adjusted to 7.0 with citric acid. The solution is then clarified and sterilized by passing the liquid through 293 mm Millipore membrane filters (or cartridge equivalents) having, typically, 1.2, 0.65, 0.45, or 0.3 micron diameter pores. The resulting sterile solution, containing from about 25 percent to 40 percent of the Factor VIII in the original plasma starting material is lyophilized in the normal manner for storage.

Variations of manufacturing technique, particularly employing refrozen cryoprecipitate or variants of Cohn Fraction I may be employed, although in such situations the yield of Factor VIII will be lessened and is dependent on its concentration in the starting material. Extraction of AHF may be carried out in other low ionic strength buffers such as Tris buffer. Cooling time may also be varied, increased or performed repetitively with some further aggregation of fibrinogen without departing from the invention. Likewise, extraction time can be increased to up to 24 hours within the procedure described.

The resultant product can be stored at +5° C. for long periods of time, at least one year and reconstituted in distilled water or physiologic saline. Because of its relatively low fibrinogen content and higher albumin content, it goes into solution very quickly. Since the entire processing time is very short compared to other methods of manufacture from the time that the bags of plasma are opened, bacterial growth is limited. The fact that the extraction is carried out in distilled water decreases the amount of fibrinogen and gamma globulins which go into solution. By cooling at 2° C., selective precipitation of excessive fibrinogen and its denatured and degraded products and isohemagglutinins (macroglobulins) occurs without measurable loss of AHF. In addition, the heavy flocculent precipitate of fibrinogen probably entraps any pyrogenic material present and reduces amounts of hepatitis associated antigen (HAA or hepatitis virus). This results in a product purified thirty to sixty times, over plasma, and very low in fibrinogen and "saline" isohemagglutinins. If desired, this product can be further purified and concentrated by known procedures or new procedures. In an exemplary new procedure, Factor VIII preparation of extremely high purity may be manufactured by an additional step which includes the addition of 3-6% polyol (PEG or pluronic[10]) and then cooling again for 1-2 hours at 0°-2° C. See entry No. (7), Table I. One great advantage of this invention is that the extremely pure AHF can be produced in less than eight hours, as compared with two to three times that long experienced with prior procedures.

The example given before is the optimum procedure presently known for carrying out the invention. It will be apparent, however, that the invention may be practiced through the application of conventional processing techniques and materials to the principle of the invention. For example, while it is generally not economically practicable to start with less than about 100 liters of plasma, or cryoprecipitate from this amount of plasma, there is obviously no criticality to either the upper of lower volume values given in the example and variations by fifty percent or so in these values would not effect the inventon. The procedures in the optimum example are carried out using well-known and readily available equipment, such as the Sharpless centrifuge, the Waring blender, etc., but all will recognize that these steps per se, in isolation from the inventive principle, and the equipment involved are not critical and great variation can be made within the invention within the discretion of the operator, depending upon available manpower, equipment, etc. Adsorption of aluminum hydroxide is, per se, a well-known step and not critical to the inventive concept. Considerable discretion may be exercised in carrying out this step through the substitution of other adsorbents, etc., or the accomplishment of the same objective through an equivalent step or simply omitting it. Once the supernatant liquid, containing the Factor VIII in high recovery, is obtained, it is treated in the conventional manner for storage and reconstitution; e.g., it is clarified and sterilized, through standard micropore filtration, lyophilized to concentrate the Factor VIII into a small, easily storable volume, and reconstituted using conventional liquids, e.g. pyrogen-free water or physiologic saline.

The invention is limited by the claims set forth hereinafter, and not by the specific details of the exemplary procedure set forth in the specification as the best mode.

REFERENCES CITED IN THE SPECIFICATION

1. Wickerhauser, M.: Large scale fractionation of Factor VIII—Concentrate from cryoethenol precipitate. *Thromb, Diath, Haemorrh.* 43:165, 1971
2. Hershgold, E. J., Pool, J. G., and apperhagen, A. R. The potent antihemophilic concentrate derived from a cold insoluble fraction of human plasma; Characterization and further data on preparation and clinical trial. *J. Lab. Clin. Med.,* 67: 23, 1966
3. Hershgold, E. J., Davison, A. M., & Janzen, M. E. Isolation and some chemical properties of human Factor VIII (antihemophilic factor). *J. Lab. Clin. Med.,* 77: 185, 1971
4. Shanbrom, E. & Fekete, L. Production of stable high potency human AHF using polyethylene glycol and glycine to fractionate a cryoprecipitate of AHF concentrate. U.S. Pat. No. 3,631,018, Dec. 28, 1971.
5. James, H. L. and Wickerhauser, M.: Development of large scale fractionation methods. Vox Sang. 23:401, 1972
6. Sgouris, J. T. and Wickerhauser, M.: Use of frozen cryoprecipitate for the preparation of clinical Factor VIII concentrate. *Transfusion* 13:399, 1973
7. Recent Advances in Hemophilia. *Ann. N. Y. Acad. Sci.* 240, 1-426, 1975.
8. Pool, J. G. Recent chapters in the Factor VIII saga: perils of a protein. *West. J. of Med.* 122:406, 1975
9. Fekete, L. F. and Holst, S. L. Stabilization of AHF using Heparin. U.S. Pat. No. 3,803,115, Apr. 9, 1974
10. Alpha-hydro-omega-hydroxy-poly(oxyethylene)-poly(oxypropylene) poly(oxyethyene) block copolymer, *BASF-Wyandatte Corp.: The Wonderful World of Pluronic Polyols,* 1971. PEG is the abbreviation for polyethylene glycol.

What is claimed is:

1. The method of concentrating and purifying Factor VIII consisting essentially of the steps of:
    collecting cryoprecipitate from about 100 or more liters of frozen plasma;
    extracting the cryoprecipitate thus collected in from about 2 to about 3 volumes of pyrogen-free water at about 25° C. to 30° C. and about pH 7 for from about 30 to about 60 minutes;
    removing lipids, denatured proteins and prothrombin complex from the extract solution by adsorption:
    precipitating fibrinogen its denatured and degraded products, without removal of significant amounts of Factor VIII from the resulting low ionic strength liquid extract by cooling the liquid to from about 1° C. to about 2° C. for from about one-half hour to about 2 hours;
    separating, stabilizing, clarifying and sterilizing the supernatant liquid containing about eighty percent or more of the Factor VIII in the starting material;
    lyophilizing the stabilized supernatant liquid to produce a Factor VIII concentrate which can be stored for long periods of time and which can be easily reconstituted by dissolution in distilled water or physiologic saline.

* * * * *

UNITED STATES PATENT AND TRADEMARK OFFICE
CERTIFICATE OF CORRECTION

PATENT NO. : 4,188,318
DATED : February 12, 1980
INVENTOR(S) : Edward Shanbrom

It is certified that error appears in the above-identified patent and that said Letters Patent are hereby corrected as shown below:

Column 3, line 8, "0.3" should be --0.5--.

Column 5, line 34, "apperhagen" should be --Papperhagen--.

Column 6, line 4, "23:401" should be --23:402--.

Signed and Sealed this

Tenth Day of June 1980

[SEAL]

Attest:

SIDNEY A. DIAMOND

Attesting Officer

Commissioner of Patents and Trademarks